(12) United States Patent
Nichols et al.

(10) Patent No.: US 10,487,317 B1
(45) Date of Patent: Nov. 26, 2019

(54) STABILIZING 5'-FLAP ENDONUCLEASE ACTIVITY

(71) Applicant: New England Biolabs, Inc., Ipswich, MA (US)

(72) Inventors: Nicole Nichols, Reading, MA (US); Gregory Patton, Peabody, MA (US); Janine Graham, Beverly, MA (US)

(73) Assignee: New England Biolabs, Inc., Ipswich, MA (US)

( * ) Notice: Subject to any disclaimer, the term of this patent is extended or adjusted under 35 U.S.C. 154(b) by 329 days.

(21) Appl. No.: 15/466,996

(22) Filed: Mar. 23, 2017

(51) Int. Cl.
*C12N 9/16* (2006.01)
*C12N 9/12* (2006.01)
*C12Q 1/6848* (2018.01)
*C12Q 1/686* (2018.01)
*C12N 15/00* (2006.01)

(52) U.S. Cl.
CPC .............. *C12N 9/16* (2013.01); *C12N 9/1252* (2013.01); *C12Q 1/686* (2013.01); *C12Q 1/6848* (2013.01); *C12Y 207/07007* (2013.01); *C12Y 301/00* (2013.01)

(58) Field of Classification Search
CPC .......... C12N 9/1252; C12Y 207/07007; C12Q 1/6848; C12Q 1/686
See application file for complete search history.

(56) References Cited

U.S. PATENT DOCUMENTS

| 2014/0030703 | A1* | 1/2014 | Fischer | .................. | C12Q 1/686 435/5 |
| 2014/0051126 | A1* | 2/2014 | Bauer | .................. | C12N 9/1252 435/91.21 |
| 2015/0166968 | A1* | 6/2015 | Wang | .................. | C12N 9/1252 435/6.11 |
| 2015/0361511 | A1* | 12/2015 | Lee | .......................... | A61K 9/19 435/5 |

FOREIGN PATENT DOCUMENTS

WO   WO2015/117040 A1   8/2015

OTHER PUBLICATIONS

Olivier, et al., Mutation Research, 573:103-10 (2005).
Rigby, et al, J. Mol. Biol., 13:237-51 (1977).

* cited by examiner

*Primary Examiner* — Teresa E Strzelecka
(74) *Attorney, Agent, or Firm* — New England Biolabs, Inc.; Harriet M. Strimpel

(57) ABSTRACT

A probe qPCR master mix is provided. In some embodiments, the master mix comprises nucleotides, an enzyme comprising a polymerase activity and a flap endonuclease activity, a chelating agent at a concentration greater than 5 µM, and a divalent cation. The relatively high concentration of chelating agent stabilizes the flap endonuclease activity during storage. As such, the polymerase and flap endonuclease activities may be substantially the same before and after storing the master mix for 7 days at 37° C.

7 Claims, 8 Drawing Sheets
(8 of 8 Drawing Sheet(s) Filed in Color)

STABILIZING 5'-FLAP ENDONUCLEASE ACTIVITY

BACKGROUND

Polymerases are commonly stored in a buffer that includes Ethylenediaminetetraacetic acid (EDTA) and a detergent. At the time of use, the enzyme in its storage buffer is diluted usually at least 10 fold when added to a reaction mix containing dNTPs, primers, probes and nucleic acid template for DNA amplification. Typically the storage buffer is designed to optimize storage of the enzyme reagents and not to optimize an amplification reaction. This is because the storage buffer is generally diluted at least 10 fold so that components that might interfere with the reaction are diluted out.

Large numbers of samples may be analyzed by probe quantitative polymerase chain reaction (probe qPCR) or reverse transcription qPCR (RT-qPCR) for clinical nucleic acid-based diagnostics and certain research projects. Examples include gene expression profiling or determining thresholds of biological material in environmental samples. An advantage of probe qPCR master mixes is that only a single dilution step is required when the master mix is added to the nucleic acid template to provide optimal reaction conditions for probe qPCR.

Master mixes differ from storage buffers containing enzyme reagents and high concentrations of glycerol for reasons that include the presence in the master mix of reagents that are common to reactions including dNTPs, magnesium ions, and in some cases, probes and primers, but never sample nucleic acid templates which are unique to each reaction. Moreover, because master mixes are typically diluted only 2 fold when added to the nucleic acid template regardless of whether the nucleic acid is in a biological fluid or a formulated buffer, all the components in the master mix should be compatible with optimal reaction conditions.

Consequently, it is desirable that a probe PCR master mix be both suitable for storage and compatible with reaction conditions for probe qPCR. The master mix should provide consistency of results and not compromise sensitivity of the reaction.

Unfortunately, the consistent activity of stored master mixes for use in probe qPCR and the associated sensitivity of the assay diminishes over time reducing confidence in the data thereby undermining the use of these preparations.

SUMMARY

The problem of loss of activity and sensitivity of stored probe qPCR master mixes has been solved as disclosed herein by among other things, the recognition that storage of probe qPCR in master mixes results in loss of flap endonuclease activity. The addition of a surprisingly high concentration of a chelating agent (corresponding to greater than 5 µM chelating agent in a 2× master mix) can both rescue the lost flap endonuclease activity and prevent its loss at the outset.

In general, the probe qPCR master mix may include (a) nucleotides for example, dGTP, dATP, dTTP, dCTP, and/or dUTP, each preferably at a concentration corresponding to a range of 0.3 mmol to 1 mmol for a 2× master mix; (b) an enzyme having both polymerase activity and a flap endonuclease activity; and a (c) a chelating agent at a concentration corresponding to greater than 5 µM in a 2× master mix; wherein the master mix does not contain nucleic acid template (i.e., no intentionally added nucleic acid template, or substantially no nucleic acid template); and the flap endonuclease activity is substantially the same before and after storing the master mix for 7 days at 37° C., or at least 200 days at −20° C. In one aspect the polymerase is present in the master mix at a concentration corresponding to a range of 0.5 units/µl to 0.01 units/µl (e.g., 0.25 to 0.025 units/µl) for a 2× master mix. In one aspect, the probe qPCR master mix includes a divalent cation wherein the divalent cation is $Mg^{2+}$ for example, $MgCl_2$ or $MgSO_4$ where the concentration may correspond to a range of 3 mM to 15 mM (in a 2× master mix). In one aspect, the qPCR master mix includes glycerol at a concentration corresponding to less than 30% (v/v) e.g., less than 20% glycerol, less than 10% glycerol, or less than 5% glycerol in a 2× master mix.

The probe qPCR master mix is provided in an effective buffer, preferably a non-naturally occurring buffer such as Tris-HCl or Tricine, preferably buffered at a pH in the range of pH 7.5 to pH 9.5. In one aspect, the qPCR master mix may be concentrated with respect to the reaction mix by 1.5×-5× or even as much as 10×, preferably 2×, so that an aliquot of predetermined volume can be added to the nucleic acid template optionally including primers and probes, if not already included in the master mix, without any additional manipulation. The amount of reagent in more dilute or more concentrated master mix is described above for a 2× master mix and adjusted accordingly.

In one aspect, the flap endonuclease activity is substantially the same before and after storing the master mix for at least 7 days for example, as long as 30 days or 6 months or 12 months at a temperature of at least −20° C. while preserving flap endonuclease activity. Additionally, flap endonuclease activity is preserved at a temperature in the range of 3° C. to 10° C., room temperature, or at approximately 37° C. which further substantiates the stability of this activity under long term storage conditions at lower temperatures. One approach to determining flap endonuclease activity is performing a probe qPCR reaction for a defined amount of template DNA and measuring fluorescence resulting from cleavage of one or more hydrolysis probes during amplification.

In general in one aspect, a method is provided that involves (a) combining a nucleic acid template with a stored buffered probe qPCR master mix described above to produce a reaction mix; (b) thermocycling the reaction mix while reading a fluorescent signal generated by cleavage of one of more probes, thereby providing an estimate of the amount of template in the reaction mix. In one aspect, the master mix is stored for a plurality of days at a temperature of at least about −20° C. (e.g., at a temperature in the range of 3° C. to 10° C., room temperature, or at approximately 37° C.), or as much as several months (e.g., at least 6 months) at approximately −20° C., prior to performing step (a).

In general in one aspect, a method is provided that includes providing a probe qPCR master mix for adding to a nucleic acid template to produce a reaction mix for performing probe qPCR, the probe qPCR master mix comprising (a) nucleotides, (b) an enzyme with polymerase and flap endonuclease activity where each enzyme activity is substantially the same after storage for 7 days at 37° C. or for at least 200 days at −20° C. as before storage, and (c) a buffer containing a chelating agent having a concentration corresponding to greater than 5 µM in a 2× master mix; and determining from the probe qPCR, the amount of the nucleic acid in the sample. One aspect of the method may include storing the master mix for a plurality of days at a temperature of at least about −20° C. prior to performing the probe qPCR.

In general, a reagent system is provided that includes a probe qPCR master mix in an effective buffer, preferably a non naturally occurring buffer such as Tris-HCl or tricine, and (a) nucleotides for example, dGTP, dATP, dTTP, dCTP and/or dUTP, each at concentration in the range of 0.3 mmol to 1 mmol for a 2× master mix; (b) an enzyme having both polymerase activity and a flap endonuclease activity; and a (c) a chelating agent at a concentration of at least 5 µM for a 2× master mix; wherein the master mix does not contain any intentionally added nucleic acid template; and the flap endonuclease activity is substantially the same before and after storing the master mix for 7 days at 37° C. or 224 days at −20° C. In one aspect, the PCR primers and the one or more probes are in separate containers. In another aspect, the PCR primers and the one or more probes are in the same container. In another aspect, the reagent system further comprising a nucleic acid template.

BRIEF DESCRIPTION OF THE FIGURES

The patent or application file contains at least one drawing executed in color. Copies of this patent or patent application publication with color drawing(s) will be provided by the Office upon request and payment of the necessary fee.

The skilled artisan will understand that the drawings, described below, are for illustration purposes only. The drawings are not intended to limit the scope of the present teachings in any way.

FIG. 1 A-1B shows the loss of Taq DNA polymerase activity in a 2× probe qPCR master mix upon storage.

FIG. 2A, shows results from the use of a probe qPCR master mix relying on Taq DNA polymerization activity and 5'-flap endonuclease activity preincubated at 37° C. for 7 days. Loss of qPCR signal is observed by comparison with the activity shown in FIG. 1B for a master mix stored at −20° C. for 7 days.

FIG. 2B shows results from SYBR® (Molecular Probes, Inc.) qPCR, which relies on Taq DNA polymerase's polymerization activity but not 5'-flap endonuclease activity. The 2× probe qPCR master mix was preincubated at 37° C. for 7 days and supplemented with SYBR prior to performing qPCR. The fluorescence signal was not significantly decreased.

FIG. 2C shows that addition of thermostable flap structure-specific endonuclease I (FEN1), an endonuclease that cleaves 5'-DNA flaps from branched double-stranded DNA, rescues the compromised 5'-flap endonuclease activity of Taq DNA polymerase of a 2× probe qPCR master mix preincubated at 37° C. for 23 days.

FIG. 3A shows the amounts of Tris and EDTA carried over from the gDNA input into each template dilution of the qPCR assay.

FIG. 3B shows the qPCR amplification curves for each gDNA input. Green curves represent amplification reactions containing 50 ng input gDNA (carry over of 250 µM Tris, 25 µM EDTA) while orange curves represent reactions containing 0.005 ng input gDNA (carry over of 0.025 µM Tris, 0.0025 µM EDTA). The 50 ng gDNA input and highest TE buffer carryover, rescued 5'-flap endonuclease activity of Taq DNA polymerase, as indicated by the fluorescence signal (y-axis). Impaired activity was observed for the four lowest gDNA input concentrations (containing the lowest concentrations of Tris and EDTA; blue, pink, purple and orange curves).

FIG. 5A shows the effect of supplementing the amplification reactions with 750 µM Tris, pH 8.0. No recovery of 5'-flap endonuclease activity of Taq DNA polymerase was observed.

FIG. 5B shows the effect of supplementing the amplification reactions with 75 µM EDTA. Recovery of 5'-flap endonuclease activity of Taq DNA polymerase was observed.

FIG. 6A shows the qPCR amplification curves following incubation of the 2× hydrolysis probe-based qPCR master mix containing 54 µM EDTA at −20° C. for 23 days.

FIG. 6B shows the qPCR amplification curves following incubation of the 2× hydrolysis probe-based qPCR master mix containing 54 µM EDTA at 37° C. for 23 days. No significant loss of activity was observed.

DESCRIPTION OF EMBODIMENTS

Figure 1A:
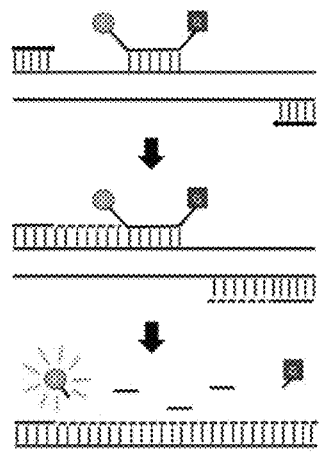
FIG. 1A schematically illustrates how a fluorescent signal is generated in a hydrolysis probe qPCR assay. The signal is produced by the separation of fluorescent dye from quencher that occurs when the labeled probe is hydrolyzed by the 5'-flap endonuclease activity of a polymerase, during extension of a complementary strand along a target template. Fluorescence can then be measured in a qPCR instrument. Both of Taq DNA polymerase's activities (polymerization and 5' flap endonuclease activity) are required to generate a fluorescence signal.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As will be described in greater detail below, it has been found that if a probe qPCR master mix is stored for a prolonged period of time at 37° C. (days) or at −20° C. (months), the flap endonuclease activity, but not the polymerase activity, of the DNA polymerase in the master mix significantly decreases so as to compromise the reliability and the sensitivity of a probe qPCR analysis. Surprisingly, this effect can be reversed by the addition of a chelating agent such as EDTA to the master mix. While not wishing to be limited by theory, it is believed that the chelating agent may bind with a divalent ion (other than $Mg^{2+}$) that selectively inhibits the flap endonuclease activity of the polymerase.

The chelating agent can stabilize the flap activity of the polymerase when the master mix containing greater than 5 µM of chelating agent (2× master mix) at elevated temperature, (e.g., at a temperature in the range of 3° C. to 10° C., room temperature, or at approximately 37° C.) for several days, weeks or even months. In some embodiments, the master mix can be stored for several months or years at −20° C. without significant loss of activity.

As used herein, the term "buffered probe qPCR master mix" refers to a premixed, ready-to-use aqueous solution suitable for probe qPCR that is buffered, e.g., by a buffering agent such as Tris, and minimally contains the following components: (i) a DNA polymerase that has both a polymerase activity and a flap endonuclease activity, (ii) dNTPs (i.e., dGTP, dATP, dTTP, dCTP and/or dUTP and/or analogs thereof) and (iii) a divalent cation, e.g., $Mg^{2+}$. A buffered probe qPCR master mix may also potentially contain other components that may be optional, but not required, for PCR, as well as other components that are present in the storage buffer for the polymerase (albeit at lower concentrations than in the storage buffer). NaCl, KCl, DTT, detergent (e.g., Tween) are examples of such components. A reverse transcriptase may be included in the probe qPCR master mix to convert RNA into cDNA. The reverse transcriptase may be any standard enzyme capable of reverse transcription such as Maloney Murine leukemia virus (MMLV reverse transcriptase) and mutants thereof. A master mix can potentially contain other proteins (e.g., a DNA binding protein or other enzyme). In one embodiment, a buffered qPCR master mix does not contain any intentionally added template specific primers, probes or target nucleic acid templates (e.g., gDNA templates or, cDNA, RNA or primer extension products). In other embodiments, the buffered probe qPCR master mix contains template specific primers, and hybridization probes but substantially no target nucleic acid templates (e.g., gDNA templates or, cDNA, RNA or primer extension products). In many cases, a buffered probe qPCR master mix contains all of the necessary components for performing a probe qPCR reaction, as well as other optional components for increasing the speed, sensitivity, specificity, or signal from a qPCR reaction, excluding the PCR primers, probe and template. The term "buffered probe qPCR" is used interchangeably with the term "probe qPCR" and is intended to denote a non-naturally occurring mixture.

In use, a buffered probe qPCR master mix can be aliquoted into several reaction vessels (e.g., tubes or wells of a multi-well plate) and, as such, may have any desired volume of, e.g., at least 10 µl, 100 µl, 500 µl, 1 ml, 5 ml or 10 ml. Alternatively, pre-aliquoted 96 well plates (e.g., 2 µl-25 µl) may be used. A master mix can be at, e.g., a 2×, a 3×, a 4× or a 5× concentration relative to a qPCR reaction mix, for example.

It should be understood that concentrations of components of the qPCR master mix are provided for a 2× solution (2 fold concentration). Where the concentration of the master mix is 1.5×, 2.5×, 3×, 3.5×, 4×, 5×, or higher, then the concentration of reagents will be proportionally altered. In certain embodiments, it may be expedient to add a higher fold concentration of master mix to a dilute nucleic acid template contained in a relatively large volume. Optionally, PCR primers and hybridization probes, if not present in the master mix, are combined with the nucleic acid template. For example, in some embodiments, a master mix may be at a 2× concentration, meaning that a reaction mix of a defined volume (50 ul volume) can be made by combining a defined volume of the mix (e.g., 25 µl of the mix) with the same combined volume (i.e., 25 µl) of PCR primers, hydrolysis probe, nucleic acid template and water.

In embodiments in which the buffered probe qPCR is at a "2×" concentration, the mix may comprise dGTP, dATP, dTTP, dCTP and/or dUTP, each at concentration in the range of 200 µM to 600 µM an enzyme is at a concentration in the range of 0.1 units/µl to 0.04 units/µl.

As used herein, the term "qPCR reaction mix" contains components of buffered probe qPCR master mix (at a lower concentration than the master mix), as well as PCR primers, probe and nucleic acid template.

As used herein, the term "enzyme storage mix" contains the polymerase as well as a buffering agent, glycerol at a concentration of 40% to 60% (e.g., approximately 50% glycerol), as well as optionally EDTA and detergent. An enzyme storage mix does not contain dNTPs, PCR primers, probe, nucleic acid template or $Mg^{2+}$ ions.

As used herein, the term "chelating agent" is a substance whose molecules can form several bonds to a single metal ion, e.g., a divalent cation such as $Mg^{2+}$. EDTA is an example of a chelating agent. Examples of chelating agents expected to have a similar effect to that of EDTA include ethylene glycol bis(2-aminoethylether)-N,N,N',N'-tetraacetic acid (EGTA); diethylenetriaminepentaacetic acid (DTPA); 1,2-diaminocyclohexanetetra-acetic acid (DCTA); triethylenetetraminehexa-acetic acid (TTHA); nitrilotri-acetic acid (NTA) and 1,2-bis(o-aminophenoxy)ethane-N, N,N',N'-tetraacetic acid (BAPTA). The chelating agent may be at a concentration of greater than 5 µM, at least 10 µM, at least 15 µM or at least 20 µM in the present buffered probe qPCR master mix.

As used herein, a probe is an oligonucleotide (DNA or RNA) that is synthetic or natural in origin and is capable of hybridizing to a portion of a nucleic acid template sequence and can be removed or degraded during amplification by flap endonuclease activity. The probe may be named a hybridization probe and may be labeled. Examples of labels include, radioactive labels, and fluorophores and/or quenchers. Examples of probes include hydrolysis probes, padlock probes, molecular inversion probes, and connector inversion probes.

As used herein, the term "hydrolysis probe" refers to a nucleic acid probe having a fluor and quencher (see FIG. 1A) that hybridizes to a site in a target nucleic acid. The probe binds to the specific target sequence during the annealing step. Because of the proximity between the donor (fluor) and acceptor (quencher) on the probe, there is no fluorescence. During the extension step, the flap endonuclease activity of the polymerase hydrolyses the probe relieving the fluor from quenching effects. This fluorescence can be read by a detector. This reaction is shown in FIG. 1A.

As used herein, the term "qPCR" refers to a real time, quantitative assay that is carried out in a thermal cycler with the capacity to illuminate each sample with a beam of light of at least one specified wavelength and detect the fluorescence emitted by the excited fluorophore. Probe qPCR relies on the use of a probe (such as a hydrolysis probe) and the presence of flap endonuclease activity in the reaction mixture. The thermal cycler is also able to rapidly heat and chill samples, thereby taking advantage of the physicochemical properties of the nucleic acids and DNA polymerase. In qPCR, the thermocycling process can consist of a series of temperature changes that are generally repeated 25 to 50 times. Most commonly, qPCR uses a two-step protocol: the first step is most commonly done at approximately 95° C. and allows denaturation. The second step is typically a combined annealing/extension step resulting in polymerization reaction at a temperature often between 60° C.-72° C. Alternatively, thermocycling may include three stages: the first, at around 95° C., allows the separation of the nucleic acid's duplex strands; the second, at a temperature of around 50° C.-65° C., allows the binding of the primers with the DNA template; the third, at between 68° C.-72° C., facilitates the polymerization carried out by the DNA polymerase.

Probe qPCR methods may rely on a hydrolysis probe as discussed above. As noted above, such a probe has a fluorescent reporter and a quencher of fluorescence. The close proximity of the reporter to the quencher prevents detection of its fluorescence; breakdown of the probe by the flap endonuclease activity of the Taq polymerase breaks the reporter-quencher proximity and thus allows unquenched emission of fluorescence, which can be detected after excitation with a beam of light. An increase in the product targeted by the reporter probe at each PCR cycle therefore causes a proportional increase in fluorescence due to the breakdown of the probe and release of the reporter. Fluorescence is detected and measured in a real-time PCR machine, and its geometric increase corresponding to exponential increase of the product is used to determine the quantification cycle (Cq) in each reaction.

The term "a temperature of above −20° C. includes temperatures in the range of 3° C. to 10° C., room temperature (i.e., in the range of 15° C.-30° C.), and at approximately 37° C. Storage of a master mix for 1 day at 37° C. is equivalent to storage of the mix for approximately 32 days at −20° C.

The term "substantially the same as" means that two parameters differ by no more than 20%, no more than 10% or no more than 5%.

As used herein, the term "buffering agent", refers to an agent that allows a solution to resist changes in pH when acid or alkali is added to the solution. Examples of suitable non-naturally occurring buffering agents that may be used in the compositions, kits, and methods of the invention include, for example, Tris, HEPES, TAPS, MOPS, tricine, or MES.

The term "non-naturally occurring" refers to a composition that does not exist in nature. Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunologically tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state.

In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

In the preparation of master mixes, it is generally acknowledged that polymerase activity requires divalent cations, e.g., magnesium ions. For this reason, it is generally considered that the concentration of a chelating agent such as EDTA should be minimal. The state of the art with respect to commercial Taq polymerases is that while the enzyme should be stored at a high concentration (at least 10 times the concentration of the reaction mix) in a relatively high concentration of EDTA, this should be diluted out in a reaction mixture. As can be seen from Table 1, while EDTA may be present in as much as 100 uM in a storage mix, after dilution into the reaction mix, the concentration is significantly less than 5 μM. Descriptions of these commercial mixtures do not discuss master mixes that may vary from the reaction mixture. No details of any such commercial master mix for qPCR was identified in the art. In one example, not in Table 1, Gencraft describes a storage buffer containing EDTA which is added to the polymerase and nucleotides only in a reaction mixture for PCR.

TABLE 1

Commercial Taq polymerase with different storage and reaction conditions

| Vendor | Product Name | Storage buffer (EDTA) | Reaction buffer (EDTA) |
|---|---|---|---|
| Thermo Fisher (Waltham, MA) | Taq DNA polymerase | 0.1 mM | 0.2-0.5 μM |
| | Taq DNA polymerase (recombinant) | 0.1 mM | 0.5 μM |
| | Platinum ® Taq DNA Polymerase, Classic | 0.1 mM | 0.2-0.5 μM |
| | Platinum ® Taq DNA Polymerase, High Fidelity | 0.1 mM | 0.4 μM |
| | DreamTaq ® DNA Polymerase | 0.1 mM | 0.5 μM |
| | ThermoPrime Taq DNA Polymerase | 0.1 mM | 0.5 μM |
| | Thermo-Start Taq DNA Polymerase | 0.1 mM | 0.5 μM |
| | Red Hot Taq DNA Polymerase | 0.1 mM | 0.5 μM |
| | Maxima Hot Start Taq DNA Polymerase | 0.1 mM | 0.5-0.8 μM |
| Invitrogen (Carlsbad, CA) | AccuPrime ™ Taq DNA Polymerase | 0.1 mM | 2.5 μM |
| GenScript (Piscataway, NJ) | Taq DNA Polymerase | 0.1 mM | 1 μM |
| | Green Taq DNA Polymerase | 0.1 mM | 0.5-2 μM |
| Sigma-Aldrich (St. Louis, MO) | JumpStart ™ Taq DNA Polymerase | 0.05 mM | 1 μM |
| | Taq DNA Polymerase, from *Thermus aquaticus* recombinant, expressed in *Escherichia coli* | 0.1 mM | 1 μM |

Examples of polymerases having both polymerase and flap endonuclease activity include Family A polymerases such as Taq DNA Polymerase, *E. Coli* DNA Polymerase I and Bst DNA Polymerase.

Probe qPCR master mixes as described herein may be lyophilized. The lyophilized dNTPs, magnesium ions, enzyme with flap endonuclease and polymerase activity and a chelating agent may be lyophilized in a single mixture. The lyophilized master mix may additionally include probes and primers. The lyophilized master mix may be present on a solid support such as a plastic matrix, such as a 96 well dish, or a 2D support such as a paper matrix, or a 3D matrix such as a column or in a chip such as a silica chip or in an array or microfluidic device.

The master mix with improved storage properties is here shown to be effective for qPCR. Other uses for the master mixes described herein include Invader cleavage assay (for single nucleotide polymorphism detection; see, e.g., Olivier et al, Mutation Research 2005 573:103-10), removal of damaged 5' bases in DNA library construction workflows (WO2015/117040 A1), nick translation (see, e.g., Rigby et al, J. Mol. Biol. 1977 113:237-51) and labeling DNA.

All references cited herein are incorporated by reference.

EXAMPLES

Aspects of the present teachings can be further understood in light of the following examples, which should not be construed as limiting the scope of the present teachings in any way.

Example 1: Demonstration of Loss of Flap Endonuclease Activity in a Polymerase Master Mix A 2× probe qPCR master mix (23 nM Taq DNA polymerase, 5 mM $Mg^{2+}$, 1.6 mM nucleotides, pH in the range of pH 8-pH 9) was stored at either 37° C. for 1 day or −20° C. for 7 days and was utilized to prepare reactions to amplify ACTB cDNA. Triplicate 20 µL amplification reactions containing a 5'-FAM hydrolysis probe (0.2 µM) and primers (0.4 µM) were set up across a five-log concentration range of input human cDNA template using 10 µL of a 2× probe qPCR master mix. Stocks of primers and 5'-FAM hydrolysis probe (Integrated DNA Technologies, Coralville, Iowa) were diluted and stored in water. Stock concentrations of cDNA template ranging from 2.5 ng/µL to 0.00025 ng/µL were prepared by diluting 10 ng/µL human cDNA to 2.5 ng/µL and subsequently performing four 10-fold serial dilutions in water. An aliquot of 2 µL of each cDNA stock concentration was added to the amplification reactions such that the final template concentration of cDNA ranged from 5 ng to 0.0005 ng. Amplification was monitored in the FAM channel of a qPCR instrument (Bio-Rad, Hercules, Calif.) by the appearance of fluorescence (y-axis, RFU) over 45 amplification cycles (x-axis). Conditions for amplification were as follows: 95° C. for 1 minute, 45 cycles of [95° C. for 15 seconds, 60° C. for 30 seconds, fluorescence read]. The resulting amplification curves (see FIG. 1B) showed a reduced gain of fluorescence for a given cycle number that reflects the loss of enzyme activity in the master mix stored at 37° C. for 1 day compared with storage at −20° C. for 7 days. Storage for at 37° C. for 1 day approximates to 32 days at −20° C. according to the Arrhenius equation assuming first order decay.

Example 2: Flap Endonuclease Activity but not Polymerase Activity is Impaired

Figure 1B:
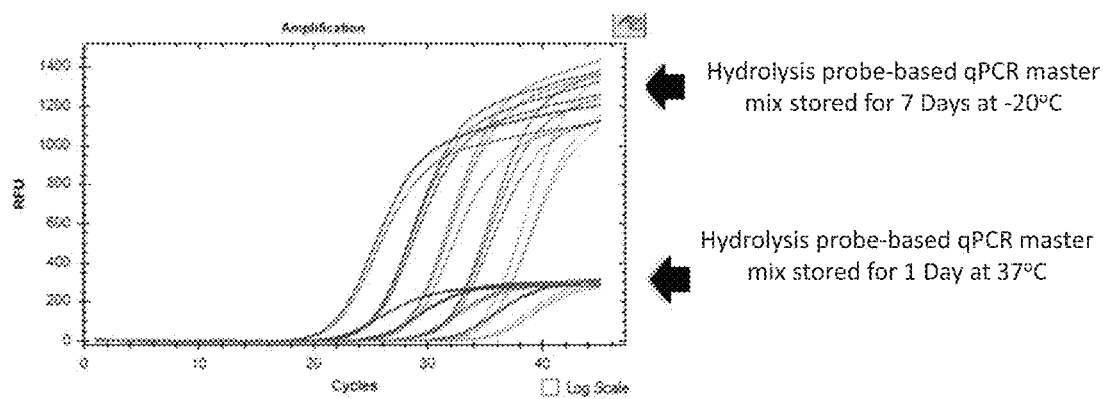
FIG. 1B shows that storage of a 2× probe qPCR master mix at 37° C. for 1 day results in a reduced gain of fluorescence signal in qPCR when compared to storage at 20° C. for 7 days. A reduced gain of fluorescence (y-axis) for a given cycle number (x-axis) reflects loss of enzyme activity. Concentration of human cDNA template in the amplification reactions is represented by different colored curves (green, 5 ng input; blue, 0.5 ng input; pink, 0.05 ng input; purple, 0.005 ng input; orange, 0.0005 ng input).
Figure 2A:
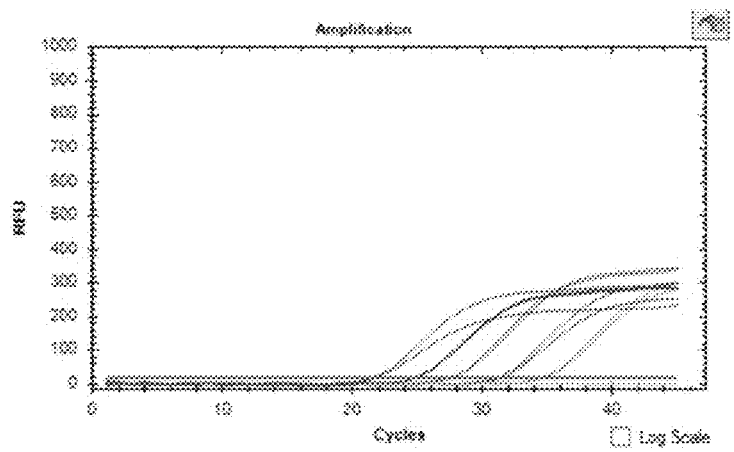
FIG. 2A-2C shows that the flap endonuclease activity but not polymerase activity of Taq DNA polymerase is impaired, as determined by the fluorescence signal (y-axis) over different cycle numbers (x-axis) at each concentration of cDNA input ranging from 5 ng-0.0005 ng. Resulting amplification curves are colored by cDNA input as outlined in FIG. 1B.
Figure 2B:
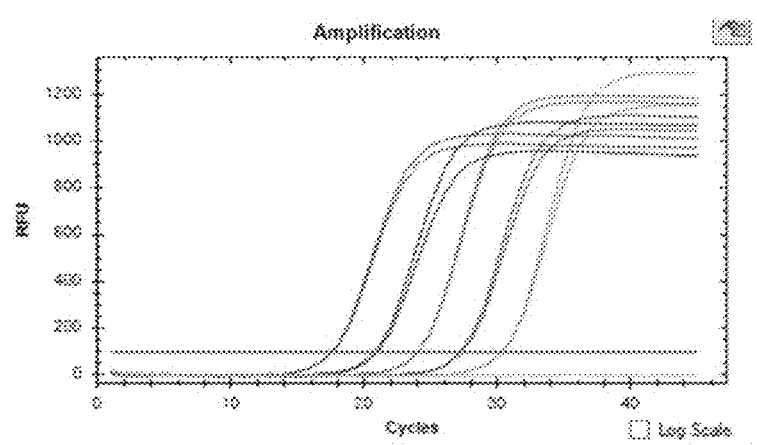
Figure 2C:
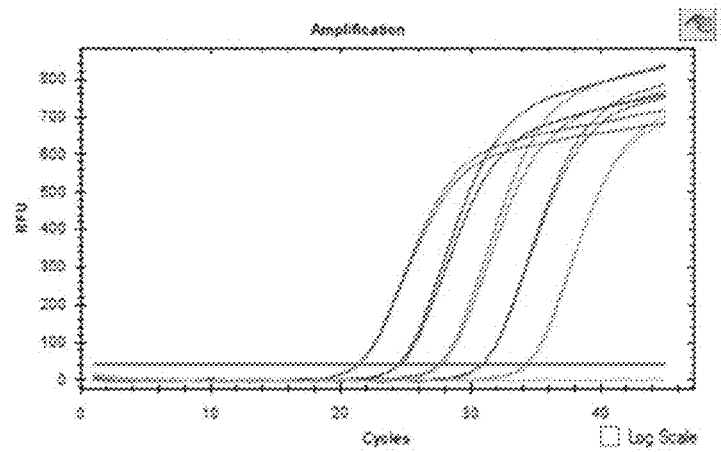

A 2× probe qPCR master mix (described in Example 1) was preincubated at 37° C. for 7 days prior to performing the ACTB cDNA qPCR assay described in Example 1. The resulting amplification curves (see FIG. 2A) showed a reduced fluorescence signal due to loss of enzyme activity. When the reaction was supplemented with 0.2 nM of a double-stranded DNA intercalating dye [SYBR Green, (Thermo Fisher Scientific, Waltham, Mass.)] in place of the hydrolysis probe to monitor the accumulation of double-stranded target DNA (independent of flap endonuclease activity), the fluorescence signal was not significantly decreased (FIG. 2B) when compared to storage at −20° C. for 7 days (FIG. 1B). This suggests that the decrease in fluorescence signal is not caused by the 5'-3' polymerization activity of Taq DNA polymerase. When a 2× probe qPCR master mix (described in Example 1) preincubated at 37° C. for 23 days was supplemented with 9.6 units of thermostable FEN1 (New England Biolabs, Ipswich, Mass.) in the ACTB cDNA qPCR assay described in Example 1, a majority of fluorescence signal was restored (FIG. 2C). A majority of 5' flap endonuclease activity was rescued through enzymatic action of FEN1 indicating the flap endonuclease activity of Taq DNA polymerase was impaired.

Figure 3A:
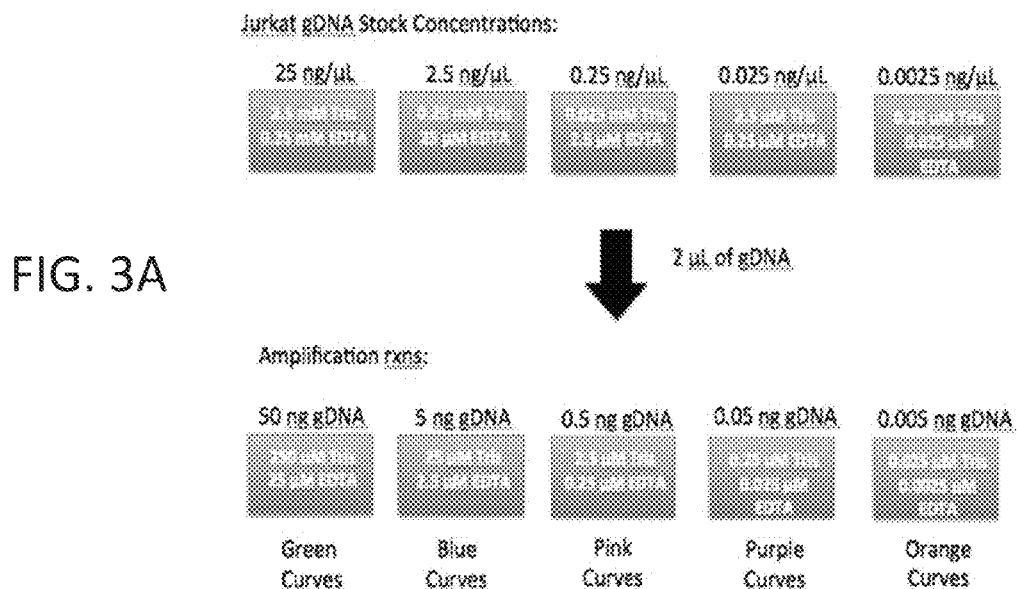
FIG. 3A-3B shows rescue of 5' flap endonuclease activity of Taq DNA polymerase by 10 mM Tris pH 8.0, 1 mM EDTA buffer as determined by the fluorescence signal (y-axis) over different cycle numbers (x-axis) for each concentration of Jurkat genomic DNA (gDNA) input ranging from 50 ng-0.005 ng. A 2× probe qPCR master mix preincubated for 37° C. for 7 days was tested in qPCR using gDNA, stored in TE buffer, and diluted in water.
Figure 3B:
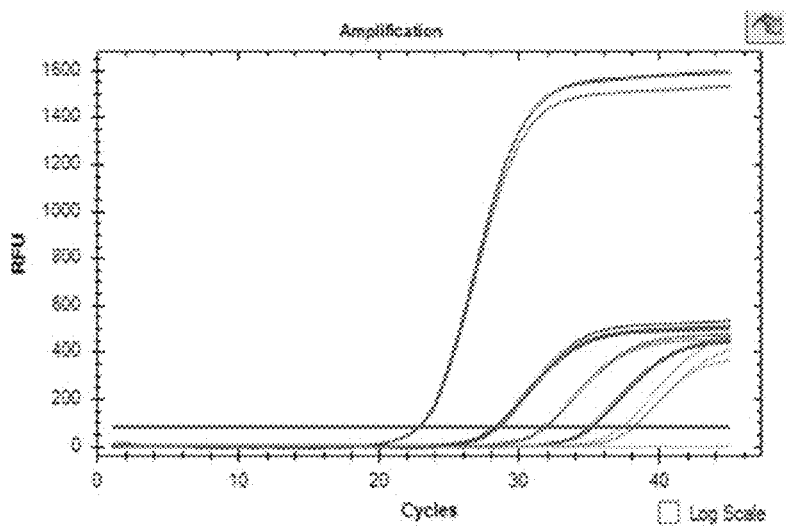
Figure 4:
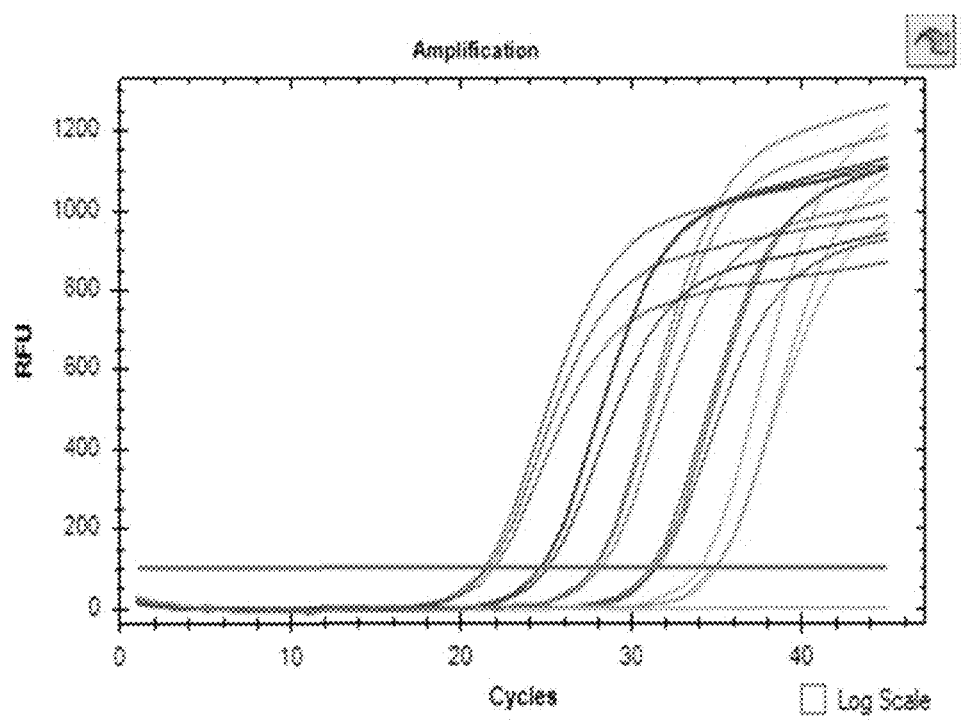
FIG. 4 shows that Tris EDTA (TE) buffer restores 5'-flap endonuclease activity of Taq DNA polymerase as determined by the fluorescence signal (y-axis) over different cycle numbers (x-axis) for a concentration of cDNA template ranging from 5 ng-0.0005 ng. A 2× probe qPCR master mix preincubated at 37° C. for 14 days was tested in qPCR using human cDNA diluted in TE buffer (carry over of 750 µM Tris, 75 µM EDTA). Amplification curves are colored by cDNA input as outlined in FIG. 1B. The fluorescence signal (y-axis) was recovered for each cDNA input indicating either Tris or EDTA carried over from cDNA template addition was responsible for rescuing the 5'-flap endonuclease activity of Taq DNA polymerase.

Example 3: Rescue of 5' Flap Endonuclease Activity of Taq DNA Polymerase by Tris EDTA (TE) Buffer A 2× probe qPCR master mix (described in Example 1) preincubated for 37° C. for 7 days was tested in the ACTB qPCR assay using Jurkat gDNA as template. Stock concentrations of gDNA template ranging from 25 ng/µL to 0.0025 ng/µL were prepared by diluting 100 ng/µL gDNA, stored in TE buffer, to 25 ng/µL and subsequently performing four 10-fold serial dilutions in water. An aliquot of 2 µL of each gDNA stock concentration was added to the amplification reactions such that the final concentration of gDNA ranged from 50 ng to 0.005 ng. Carryover concentration of Tris EDTA from gDNA template addition ranged from 250 µM Tris, 25 µM EDTA to 0.025 µM Tris, 0.0025 µM EDTA, as shown in FIG. 3A. The ACTB qPCR assay was subsequently performed as outlined in Example 1. No loss of fluorescence signal was observed for the green amplification curves (50 ng gDNA input, carry over of 250 µM Tris, 25 µM EDTA) when qPCR was performed, as shown in FIG. 3B. Impaired activity was observed for the four lowest gDNA input concentrations (containing the lowest concentrations of Tris and EDTA; blue, pink, purple and orange curves). This data demonstrates that TE buffer carried over into the qPCR assay from the addition of gDNA template recovers 5'-flap endonuclease activity of Taq DNA polymerase.

Example 4: Tris EDTA Buffer Restores 5'-Flap Endonuclease Activity of Taq DNA Polymerase A 2× probe qPCR master mix (described in Example 1) preincubated at 37° C. for 14 days was tested in the ACTB qPCR assay using human cDNA diluted in TE buffer. Stock concentrations of cDNA template ranging from 2.5 ng/µL to 0.00025 ng/µL were prepared by diluting 10 ng/µL human cDNA to 2.5 ng/µL and subsequently performing four 10-fold serial dilutions in TE buffer. An aliquot of 2 µL of each cDNA stock concentration was added to the amplification reactions such that the final concentration of cDNA ranged from 5 ng to 0.0005 ng. This resulted in a supplemental concentration of at least 750 µM Tris, pH 8.0 and 75 µM EDTA in the amplification reactions. Amplification reactions for ACTB were repeated as described in Example 1. The fluorescence signal was recovered for each cDNA input indicating either Tris or EDTA was responsible for rescuing the 5'-flap endonuclease activity of Taq DNA polymerase.

Figure 5A:
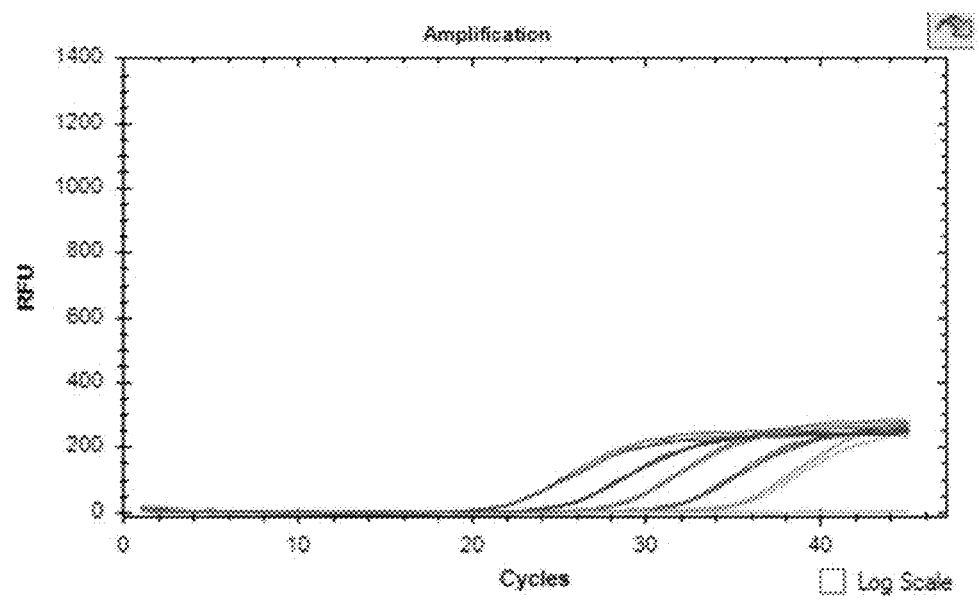
FIG. 5A-5B show that EDTA alone restores 5'-flap endonuclease activity of Taq DNA polymerase as determined by the fluorescence signal (y-axis) over different cycle numbers (x-axis) for a concentration of cDNA template ranging from 5 ng-0.0005 ng. A 2× probe qPCR master mix preincubated at 37° C. for 7 days was tested in qPCR with human cDNA template diluted in water. Amplification reactions were supplemented with either Tris or EDTA. Resulting amplification curves are colored by cDNA input as outlined in FIG. 1B.
Figure 5B:
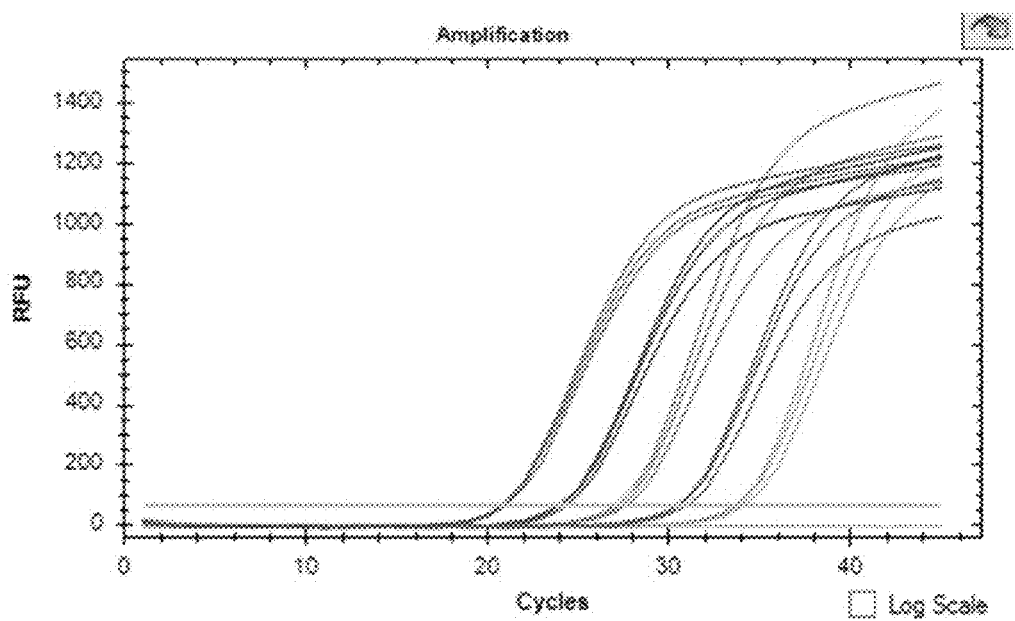

Example 5: EDTA Alone Restores 5'-Flap Endonuclease Activity of Taq DNA Polymerase A 2× probe qPCR master mix (described in Example 1) preincubated at 37° C. for 7 days was tested in the ACTB qPCR assay as described in Example 1, and reactions were supplemented with either 750 µM Tris, pH 8.0 or 75 µM EDTA. No effect on 5'-flap endonuclease activity of Taq DNA polymerase was observed from the addition of 750 µM Tris, pH 8.0 (FIG. 5A), while recovery of 5'-flap endonuclease activity of Taq DNA polymerase was observed in the presence of 75 µM EDTA (FIG. 5B).

Figure 6A:
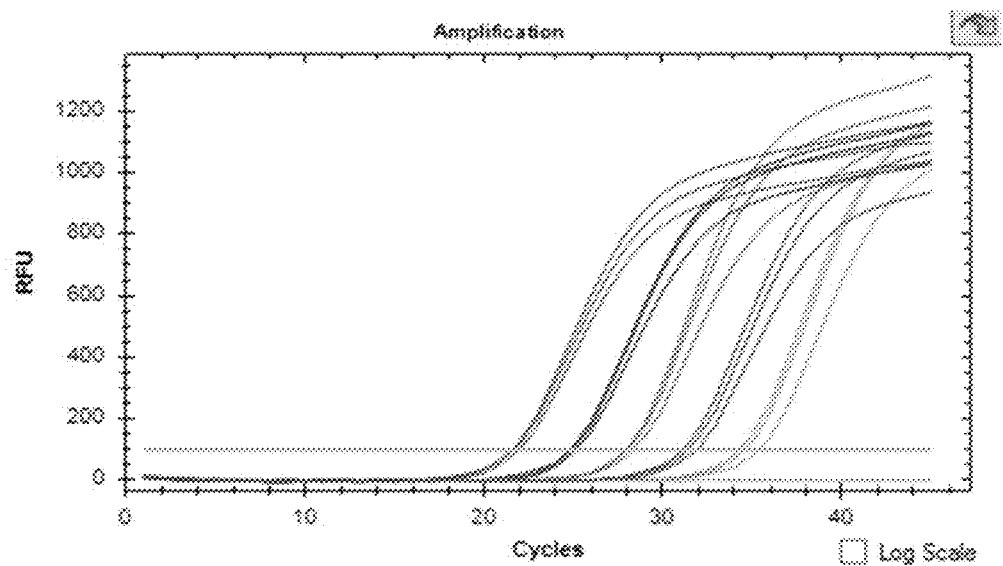
FIG. 6A-6B shows that EDTA prevents the loss of 5'-flap endonuclease activity of Taq DNA polymerase as determined by the fluorescence signal (y-axis) over different cycle numbers (x-axis) for each concentration of cDNA template ranging from 5 ng-0.0005 ng. A 2× probe qPCR master mix containing 54 µM of EDTA was incubated at 37° C. for 23 days and assayed in qPCR using human cDNA template diluted in water. No loss of fluorescence signal was observed indicating the presence of EDTA at 54 µM (in a 2× master mix) was sufficient to prevent the loss of 5'-flap endonuclease activity of Taq. Amplification curves are colored by cDNA input as outlined in FIG. 1B.
Figure 6B:
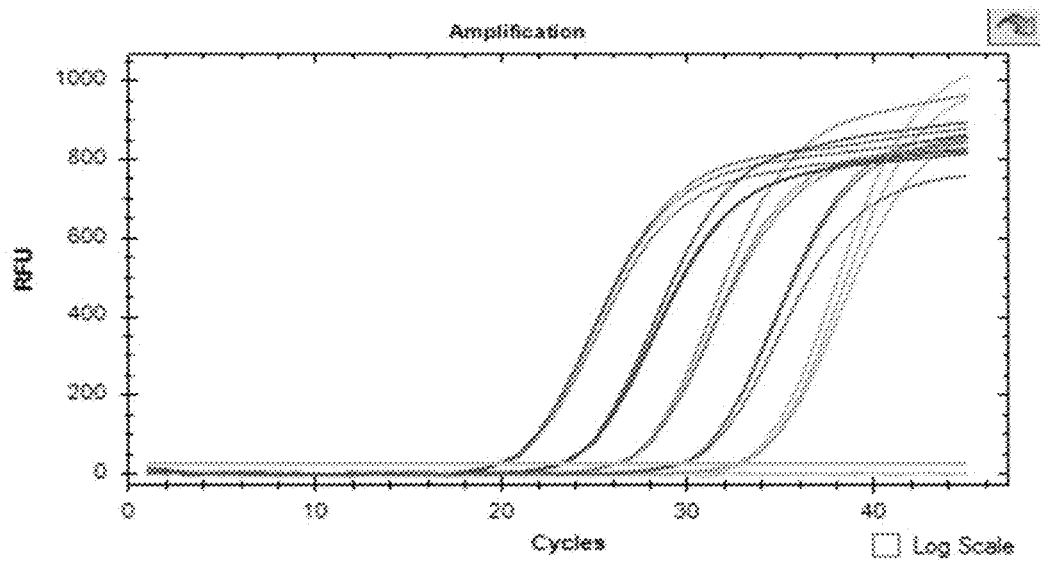

Example 6: EDTA Prevents the Loss of 5'-Flap Endonuclease Activity of Taq DNA Polymerase A 2× probe qPCR master mix (23 nM Taq DNA polymerase, 5 mM $Mg^{2+}$ and 0.4 mM each dNTP, 54 µM EDTA, pH in the range of pH 8-pH 9) was incubated at either −20° C. or 37° C. for 23 days and assayed in the ACTB qPCR assay as outlined in Example 1. No loss of fluorescence signal was observed for the 2× hydrolysis probe-based qPCR master mix stored at 37° C. indicating the presence of the chelating agent EDTA at 54 µM was sufficient to prevent the loss of 5'-flap endonuclease activity of Taq DNA polymerase. The results of these assays are shown in FIG. 6A-6B.

Example 7: Loss of 5'-Flap Endonuclease Activity of Taq DNA Polymerase in a PCR Master Mix Stored at −20° C.

Figure 7:
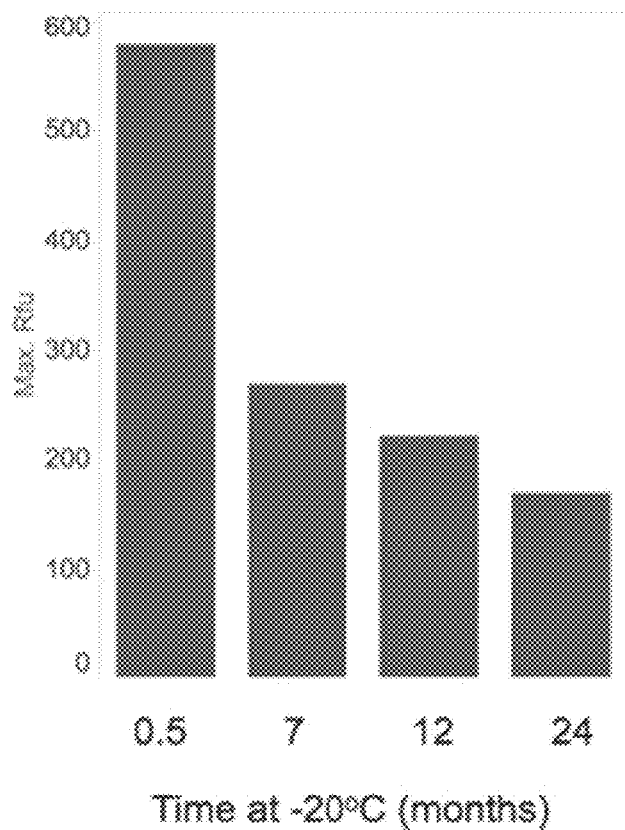
FIG. 7 shows loss of 5'-flap endonuclease activity of a Taq DNA polymerase 2× master mix upon storage at −20° C. as indicated by a decrease of maximum fluorescence signal (y-axis) in qPCR with increasing storage time at −20° C. (x-axis).
Figure 8:
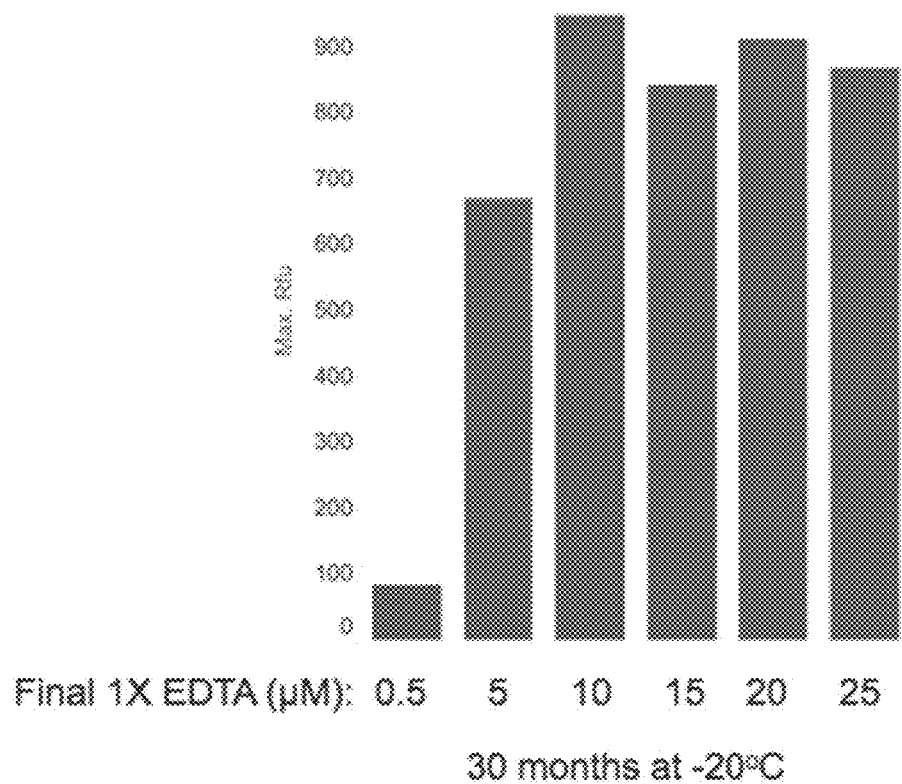
FIG. 8 shows that EDTA rescues 5'-flap endonuclease activity of a Taq DNA polymerase 2× master mix following storage at −20° C. as indicated by the maximum fluorescence signal generated in qPCR. A Taq DNA polymerase 2× master mix stored at −20° C. for 30 months was tested in qPCR at a fixed cDNA input (0.02 ng) and increasing supplemental EDTA concentrations resulting in a final EDTA concentration range of 0.5 µM to 25 µM. A final concentration of 5 µM of EDTA was sufficient to rescue the 5'-flap endonuclease activity and restore the fluorescence signal.

A Taq DNA polymerase 2×PCR master mix (5.8 nM Taq DNA polymerase, 3 mM $Mg^{2+}$, 0.4 mM each dNTP, pH in the range of pH 8-pH 9) was stored at −20° C. for up to 24 months and evaluated in the ACTB qPCR assay as described in Example 1. Maximum fluorescence signal decreased with increased storage time at −20° C. (FIG. 7), indicating loss of 5'-flap endonuclease activity of Taq DNA polymerase in the absence of additional EDTA, even at lower storage temperatures.

Example 8: EDTA Rescues 5'-Flap Endonuclease Activity of Taq DNA Polymerase in a PCR Master Mix Stored at −20° C.

A Taq DNA polymerase 2×PCR master mix (described in Example 7) stored at −20° C. for 30 months was tested in the ACTB qPCR assay at a fixed cDNA input (0.02 ng) in the presence of increasing supplemental EDTA concentrations (final concentration ranged from 0.5 µM to 25 µM). A stock concentration of cDNA template (0.01 ng/µL) was prepared by diluting 10 ng/µL human cDNA to 1.0 ng/µL and subsequently performing two 10-fold serial dilutions in water. An aliquot of 2 µL of was added to the amplification reactions such that the final concentration of cDNA was 0.02 ng. The ACTB qPCR assay was then performed as described in Example 1. A final concentration of 5 µM of EDTA was sufficient to rescue the 5'-flap endonuclease activity and restore the fluorescence signal.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations where it is desirable to examine analytes. Accordingly, the claims set forth below should be construed in view of the full breadth and spirit of the invention as disclosed herein.

What is claimed is:

1. A method comprising:
   (a) obtaining an enzyme composition that comprises Taq polymerase or a polymerase that has an amino acid sequence that is at least 95% identical to the amino acid sequence of Taq polymerase and has flap endonuclease activity, a chelating agent at a concentration corresponding to the activity of at least 5 uM EDTA, and dNTPs, and is capable of being stored for a plurality of days at room temperature without any significant loss of flap endonuclease activity
   (b) combining an enzyme composition with PCR primers, a template and a hydrolysis probe that comprises a fluorophore and a quencher to produce a reaction mix;
   (c) thermocycling the reaction mix; and
   (d) reading a fluorescent signal generated by cleavage of the hydrolysis probe by the flap endonuclease activity of the polymerase.

2. The method of claim 1, wherein the composition comprises dGTP, dATP, dTTP and dCTP and optionally dUTP.

3. The method of claim 1, wherein the composition further comprises $Mg^{2+}$.

4. The method of claim 1, wherein the composition comprises glycerol at a concentration of less than 30% (v/v).

5. The method of claim 1, wherein the composition is buffered by Tris-HCl or tricine.

6. The method of claim 1, wherein the reaction mix is subjected to 25-50 thermocycles in step (c).

7. The method of claim 6, wherein cleavage of the hydrolysis probe is read in each cycle.

* * * * *